(12) United States Patent
Liu et al.

(10) Patent No.: US 12,399,166 B1
(45) Date of Patent: Aug. 26, 2025

(54) METHOD FOR CONTROLLING SOIL AND WATER LOSS IN WIND-WATER COMPLEX EROSION REGION

(71) Applicant: China Institute of Water Resources and Hydropower Research, Beijing (CN)

(72) Inventors: Guangquan Liu, Beijing (CN); Xiaoning Tu, Beijing (CN); Ning Ai, Yan'an (CN); Liu Liu, Beijing (CN); Yingfei Bai, Yan'an (CN); Pengfei Du, Beijing (CN); Zhimin Zhang, Beijing (CN); Puhang Li, Xi'an (CN); Yan Gao, Beijing (CN); Jian Hou, Ordos (CN)

(73) Assignee: China Institute of Water Resources and Hydropower Research, Beijing (CN)

( * ) Notice: Subject to any disclaimer, the term of this patent is extended or adjusted under 35 U.S.C. 154(b) by 0 days.

(21) Appl. No.: 19/215,889

(22) Filed: May 22, 2025

(30) Foreign Application Priority Data

Jun. 27, 2024 (CN) .......................... 202410842164.2

(51) Int. Cl.
*G01N 17/00* (2006.01)
*A01B 79/02* (2006.01)
(Continued)

(52) U.S. Cl.
CPC ....... *G01N 33/246* (2013.01); *G01N 33/0098* (2013.01)

(58) Field of Classification Search
CPC .. G01N 33/246; G01N 33/24; G01N 33/0098; G01N 33/243; G01N 33/241;
(Continued)

(56) References Cited

FOREIGN PATENT DOCUMENTS

CN 104007248 A 8/2014
CN 109856368 A 6/2019
(Continued)

OTHER PUBLICATIONS

Cheng Hu et al., Comparative analysis of soil reinforcement and anti-erosion capacity of slope protection plants in land-water ecotone, Chinese Journal of Soil and Water Conservation Science, Mar. 31, 2024(Mar. 31, 2024), pp. 44053.
(Continued)

*Primary Examiner* — Jeffrey P Aiello
(74) *Attorney, Agent, or Firm* — Birchwood IP

(57) ABSTRACT

Disclosed is a method for controlling soil and water loss in a wind-water complex erosion region, which includes: randomly selecting a data acquisition reference point in a historical control area and acquiring a soil sample; detecting soil data of different soil layers on the soil sample, including soil viscosity, moisture content and organic matter content; selecting a plant sample, calculating a solid-binding coefficient of the plant sample and selecting an optimal soil-binding plant; fitting a relationship model; acquiring a control soil sample in a target control area of the wind-water complex erosion region, calculating a flatness and a soil and water loss coefficient u; setting a soil and water loss coefficient threshold $u_{threshold}$; and setting a planting density and optimal soil-binding plant type in the target control area. The present invention achieves the optimal soil and water loss control effect by considering soil-binding effects of different plants from multiple aspects.

3 Claims, 1 Drawing Sheet

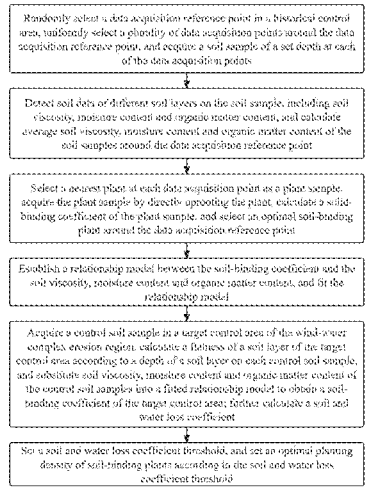

(51) Int. Cl.
*G01N 33/00* (2006.01)
*G01N 33/24* (2006.01)

(58) Field of Classification Search
CPC ... G01N 2021/1797; G01N 2021/1793; G01N 2021/1795; G06Q 10/0637; G06Q 10/0639; G06Q 50/26; G06Q 50/02; G05B 23/024; G05B 23/0281; Y02P 90/80; G06F 17/18; G06F 18/21; G06N 20/00; G06N 3/006; G06N 3/02; G06N 3/088; G06N 3/042; G06V 20/188; G06V 20/182; G06V 20/194; G06V 10/70; H04W 4/38; Y10S 47/00; Y10S 47/10; Y10S 47/905; B09C 1/105; Y02A 20/402; G01W 2201/00; G01W 2203/00
USPC ............. 47/59 R, 64, 1.43, DIG. 6; 356/301, 356/139.1; 702/2, 188, 23, 19, 30, 32, 1
See application file for complete search history.

(56) References Cited

FOREIGN PATENT DOCUMENTS

| CN | 114971234 A | * | 8/2022 | ....... G06Q 10/06393 |
| CN | 118052476 B | | 5/2024 | |
| CN | 118195164 A | | 6/2024 | |
| CN | 118362710 A | * | 7/2024 | ............. G01D 21/02 |
| CN | 118534086 A | * | 8/2024 | ............. G01D 21/02 |
| CN | 118586727 A | * | 9/2024 | ......... G06F 18/2135 |
| WO | WO-2024091715 A1 | * | 5/2024 | ............. G06N 20/00 |

OTHER PUBLICATIONS

Li Ruofan et al., Soil infiltration characteristics and simulation of different eroded degrees in the black soil region of Northeast China, Chinese Journal of Soil and Water Conservation Science, Feb. 28, 2024 (Feb. 28, 2024), Full Text.

* cited by examiner

Randomly select a data acquisition reference point in a historical control area, uniformly select a plurality of data acquisition points around the data acquisition reference point, and acquire a soil sample of a set depth at each of the data acquisition points

↓

Detect soil data of different soil layers on the soil sample, including soil viscosity, moisture content and organic matter content, and calculate average soil viscosity, moisture content and organic matter content of the soil samples around the data acquisition reference point

↓

Select a nearest plant at each data acquisition point as a plant sample, acquire the plant sample by directly uprooting the plant, calculate a solid-binding coefficient of the plant sample, and select an optimal soil-binding plant around the data acquisition reference point

↓

Establish a relationship model between the soil-binding coefficient and the soil viscosity, moisture content and organic matter content, and fit the relationship model

↓

Acquire a control soil sample in a target control area of the wind-water complex erosion region, calculate a flatness of a soil layer of the target control area according to a depth of a soil layer on each control soil sample, and substitute soil viscosity, moisture content and organic matter content of the control soil samples into a fitted relationship model to obtain a soil-binding coefficient of the target control area; further calculate a soil and water loss coefficient

↓

Set a soil and water loss coefficient threshold, and set an optimal planting density of soil-binding plants according to the soil and water loss coefficient threshold

METHOD FOR CONTROLLING SOIL AND WATER LOSS IN WIND-WATER COMPLEX EROSION REGION

CROSS-REFERENCE TO RELATED APPLICATIONS

This application claims priority to Chinese Patent Application No. 202410842164.2, filed on Jun. 27, 2024, which is hereby incorporated by reference in its entirety.

TECHNICAL FIELD

The present invention relates to the field of soil and water loss control, and in particular, to a method for controlling soil and water loss in a wind-water complex erosion region.

BACKGROUND

Wind-water complex erosion is a common erosion process in arid and semi-arid regions, characterized by the interaction between wind and water. The combined or alternating effects of wind and water on the same erosion object (area) shape the unique erosion phenomena in the wind and water erosion interlaced area. With increasing research on wind-water complex erosion regions, efforts have also been made to address the soil and water loss in the wind-water complex erosion regions. Studies have found that the inherent soil-binding capacity of plants can effectively combat soil and water loss in wind-water complex erosion regions. However, existing control measures are mostly fragmented. The selection of plants and control methods in different regions are relatively singular, and there is a lack of evaluation and research on the effectiveness of these measures. As a result, progress in the control of soil and water loss in wind-water complex erosion regions is slow.

SUMMARY

An objective of the present invention is to provide a method for controlling soil and water loss in a wind-water complex erosion region, which solves the defects in the prior art.

To achieve the above objective, the present invention uses the following technical solutions.

A method for controlling soil and water loss in a wind-water complex erosion region includes the following steps:

S1: randomly selecting a data acquisition reference point in a historical control area, uniformly selecting a plurality of data acquisition points around the data acquisition reference point, and acquiring a soil sample of a set depth at each of the data acquisition points;

S2: detecting soil data of different soil layers on the soil sample, including soil viscosity, moisture content and organic matter content, and calculating average soil viscosity $\bar{n}$, moisture content $\bar{s}$ and organic matter content $\bar{y}$ of the soil samples around the data acquisition reference point;

S3: selecting a nearest plant at each data acquisition point as a plant sample, acquiring the plant sample by directly uprooting the plant, calculating a solid-binding coefficient of the plant sample, and selecting an optimal soil-binding plant around the data acquisition reference point;

S4: establishing a relationship model between the soil-binding coefficient and the soil viscosity, moisture content and organic matter content, and fitting the relationship model;

S5: acquiring a control soil sample in a target control area of the wind-water complex erosion region, calculating a flatness of a soil layer of the target control area according to a depth of a soil layer on each control soil sample, and substituting soil viscosity, moisture content and organic matter content of the control soil samples into a fitted relationship model to obtain a soil-binding coefficient of the target control area; further calculating a soil and water loss coefficient u;

S6: setting a soil and water loss coefficient threshold $u_{threshold}$;

if $u \geq u_{threshold}$, planting optimal soil-binding plants in the target control area according to a planting density $\rho$, and controlling the soil and water loss in the wind-water complex erosion region; and if $u < u_{threshold}$, increasing a planting density to $\rho + \Delta\rho$ to enable $u \geq u_{threshold}$, planting optimal soil-binding plants in the target control area according to the planting density $\rho + \Delta\rho$, and controlling the soil and water loss in the wind-water complex erosion region, wherein $\Delta\rho$ is an increased planting density.

Further, the step S2 specifically includes:

detecting soil data of different soil layers on the soil sample, including soil viscosity, moisture content and organic matter content, and calculating average soil viscosity $\bar{n}$, moisture content $\bar{s}$ and organic matter content $\bar{y}$ of the soil samples around the data acquisition reference point;

$$\bar{n} = \sum_{M_2}^{M} \sum_{m_1=1}^{m} n_{m_1}, \bar{s} = \sum_{M_2}^{M} \sum_{m_1=1}^{m} s_{m_1}, \bar{y}_M = \sum_{M_2}^{M} \sum_{m_1=1}^{m} y_{m_1};$$

wherein M is a quantity of data acquisition points, m is a quantity of soil layers in the soil sample, $n_{m_1}$ is soil viscosity of an $m_1{}^{th}$ soil layer in the soil sample, $m_1$ is a number of the soil layer in the soil sample, $s_{m_1}$ is soil moisture content of an $m_1{}^{th}$ soil layer in the soil sample, $y_{m_1}$ is soil organic matter content of an $m_1{}^{th}$ soil layer in the soil sample, and $M_2$ is a number of the data acquisition point around the data acquisition reference point.

Further, the step S3 specifically includes:

S31: selecting a nearest plant at each data acquisition point as a plant sample, acquiring the plant sample by directly uprooting the plant, measuring a length L and a distribution radius r of a retained root system and a weight t of soil adhering to the root system in the plant sample, and calculating a soil-binding coefficient $g_e$ of each plant sample:

$$g_e = \exp^{(L+r+t)};$$

S32: after calculating soil-binding coefficients ($g_1$, $g_2$, ..., $g_e$) of all plant samples around the data acquisition reference point, selecting a maximum value $g_{max}$ in the soil-binding coefficients ($g_1$, $g_2$, ..., $g_e$), and taking a plant sample corresponding to the maximum value $g_{max}$ as the optimal soil-binding plant around the data acquisition reference point, wherein e is a quantity of plant samples.

Further, the step S4 specifically includes:

S41: establishing a relationship model between the soil-binding coefficient and the soil viscosity n, moisture content s and organic matter content y;

$$g = k_1 n + k_2 s + k_3 y;$$

wherein $k_1$, $k_2$, $k_3$ are relationship coefficients corresponding to the soil viscosity, moisture content, and organic matter content;

S42: substituting the maximum value $g_{max}$ and the average soil viscosity $\bar{n}$, moisture content $\bar{s}$ and organic matter content $\bar{y}$ of corresponding data acquisition reference points into the relationship model, selecting at least three data acquisition reference points in the historical control area, and fitting out the relationship coefficients $k_1$, $k_2$, $k_3$ to obtain a fitted relationship model.

Further, the step S5 specifically includes:

S51: uniformly selecting $\kappa$ control reference points in the target control area of the wind-water complex erosion region, acquiring control soil samples on the control reference points, and measuring depths of soil layers sequentially descending from a surface soil layer to a highest point in the control soil samples by taking a highest point in the control reference points as a reference to obtain a soil layer depth data set:

$$\{(d_1^1, d_2^1, \ldots, d_\lambda^1)_1, (d_1^2, d_2^2, \ldots, d_\lambda^2)_2, \ldots, (d_1^\kappa, d_2^\kappa, \ldots, d_\lambda^\kappa)_\kappa\};$$

wherein $d_\lambda^\kappa$ is a depth of a $\lambda^{th}$ soil layer of a control soil sample at a $\kappa^{th}$ control reference point, and $\lambda$ a quantity of soil layers in the control soil sample;

S52: calculating a flatness p of the soil layer of the target control area by using the soil layer depth data set:

$$p = \frac{1}{\kappa} \sum_{l=1}^{\kappa} \left( \frac{1}{\lambda} \sum_{i=1}^{\lambda} \left| \frac{d_i^\kappa - \hat{d}}{\hat{d}} \right| \right);$$

wherein $d_i^\kappa$ is a depth of an $i^{th}$ soil layer of the control soil sample at the control reference point, i is a number of the soil layer in the control soil sample, I is a number of the control reference point, and $\hat{d}$ is a theoretical depth of the control soil layer;

S53: calculating average soil viscosity n', moisture content s' and organic matter content y' of control soil samples at a $\kappa^{th}$ control reference point by using the method of the step S2, substituting the average soil viscosity n', moisture content s' and organic matter content y' into the fitted relationship model, and calculating the soil-binding coefficient g' of the target control area;

S54: matching an optimal soil-binding plant around data acquisition reference points in the historical control area according to the soil-binding coefficient g', minimizing a difference between the soil-binding coefficient $g_{max}$ corresponding to the optimal soil-binding plant and the soil-binding coefficient g', and obtaining a planting density $\rho$ of the optimal soil-binding plants in the historical control area; and S55: calculating the soil and water loss coefficient u under the current planting density $\rho$:

$$u = g_{max} - \mu_1 \cdot \exp^p + \mu_2 \cdot \exp^\rho;$$

wherein $\mu_1$ is a weight coefficient of the flatness of the soil layer related to the soil and water loss, and $\mu_2$ is a weight coefficient of the plant planting density related to the soil and water loss.

The present invention has the beneficial effects as follows: the present invention is used to research the soil and water loss control in the wind-water complex erosion region; specifically, plants with the optimal soil-binding effect are selected through researching the control effect in the historical control area and matches plant types adaptive to a target control area, a planting density is set, the control effect of the plants on the target control area is evaluated according to a calculated soil and water loss coefficient, and the soil-binding effects of different plants on the target control area is considered from multiple aspects, so that the optimal soil and water loss control effect is ensured.

BRIEF DESCRIPTION OF DRAWINGS

FIG. 1 is a flow chart of a method for controlling soil and water loss in a wind-water complex erosion region.

DESCRIPTION OF EMBODIMENTS

The following description of the specific embodiments of the present invention is provided to facilitate the understanding of the present invention by those skilled in the art, however, it should be understood that the present invention is not limited to the scope of the specific embodiments, and for those of ordinary skill in the art, various changes that are made without departing from the spirit and scope of the present invention as defined and determined by the appended claims are apparent, and all inventions and creations that are made by using the concept of the present invention are within the protective scope.

As shown in FIG. 1, a method for controlling soil and water loss in a wind-water complex erosion region includes the following steps:

S1: Randomly selecting a data acquisition reference point in a historical control area, uniformly selecting a plurality of data acquisition points around the data acquisition reference point, and acquiring a soil sample of a set depth at each of the data acquisition points.

S2: Detecting soil data of different soil layers on the soil sample, including soil viscosity, moisture content and organic matter content, and calculating average soil viscosity $\bar{n}$, moisture content $\bar{s}$ and organic matter content $\bar{y}$ of the soil samples around the data acquisition reference point;

$$\bar{n} = \sum_{M_2}^{M} \sum_{m_1=1}^{m} n_{m_1}, \bar{s} = \sum_{M_2}^{M} \sum_{m_1=1}^{m} s_{m_1}, \bar{y}_M = \sum_{M_2}^{M} \sum_{m_1=1}^{m} y_{m_1};$$

wherein M is a quantity of data acquisition points, m is a quantity of soil layers in the soil sample, $n_{m_1}$ is soil viscosity of an $m_1^{th}$ soil layer in the soil sample, $m_1$ is a number of the soil layer in the soil sample, $s_{m_1}$ is soil moisture content of an $m_1^{th}$ soil layer in the soil sample, $y_{m_1}$ is soil organic matter content of an $m_1^{th}$ soil layer in the soil sample, and $M_2$ is a number of the data acquisition point around the data acquisition reference point.

The higher the soil viscosity, the less likely the soil and water loss occurs; the greater the soil moisture content, the more favorable it is for plant growth; the smaller the erosion caused by wind and sand; and the higher the organic matter content, the more conducive it is to the growth of soil-binding plants.

S3: Selecting a nearest plant at each data acquisition point as a plant sample, acquiring the plant sample by directly uprooting the plant, calculating a solid-binding coefficient of the plant sample, and selecting an optimal soil-binding plant around the data acquisition reference point; wherein the step S3 specifically includes:

S31: selecting a nearest plant at each data acquisition point as a plant sample, acquiring the plant sample by directly uprooting the plant, measuring a length L and a distribution radius r of a retained root system and a weight t of soil adhering to the root system in the plant sample, and calculating a soil-binding coefficient $g_e$ of each plant sample:

$g_e = \exp^{(L+r+t)}$;

the soil-binding effect of the plant is expressed by the soil-binding coefficient, the longer the root system of the plant sample and the wider the distribution radius, the more luxuriant the plant growth, the better the soil-binding effect, and the better the effect of resisting the soil and water loss and the wind and water complex erosion;

S32: after calculating soil-binding coefficients ($g_1$, $g_2$, ..., $g_e$) of all plant samples around the data acquisition reference point, selecting a maximum value $g_{max}$ in the soil-binding coefficients ($g_1, g_2, \ldots, g_e$), and taking a plant sample corresponding to the maximum value $g_{max}$ as the optimal soil-binding plant around the data acquisition reference point, wherein e is a quantity of plant samples.

S4: Establishing a relationship model between the soil-binding coefficient and the soil viscosity, moisture content and organic matter content, and fitting the relationship model;

wherein the step S4 specifically includes:

S41: establishing a relationship model between the soil-binding coefficient and the soil viscosity n, moisture content s and organic matter content y;

$g = k_1 n + k_2 s + k_3 y$;

wherein $k_1$, $k_2$, $k_3$ are relationship coefficients corresponding to the soil viscosity, moisture content, and organic matter content;

S42: substituting the maximum value $g_{max}$ and the average soil viscosity $\bar{n}$, moisture content $\bar{s}$ and organic matter content $\bar{y}$ of corresponding data acquisition reference points into the relationship model, selecting at least three data acquisition reference points in the historical control area, and fitting out the relationship coefficients $k_1$, $k_2$ $k_3$ to obtain a fitted relationship model.

S5: Acquiring a control soil sample in a target control area of the wind-water complex erosion region, calculating a flatness of a soil layer of the target control area according to a depth of a soil layer on each control soil sample, and substituting soil viscosity, moisture content and organic matter content of the control soil samples into a fitted relationship model to obtain a soil-binding coefficient of the target control area; further calculating a soil and water loss coefficient u; wherein the step S5 specifically includes:

S51: uniformly selecting κ control reference points in the target control area of the wind-water complex erosion region, acquiring control soil samples on the control reference points, and measuring depths of soil layers sequentially descending from a surface soil layer to a highest point in the control soil samples by taking a highest point in the control reference points as a reference to obtain a soil layer depth data set:

$\{(d_1^1, d_2^1, \ldots, d_\lambda^1)_1, (d_1^2, d_2^2, \ldots, d_\lambda^2)_2, \ldots, (d_1^\kappa, d_2^\kappa, \ldots, d_\lambda^\kappa)_\kappa\}$;

wherein $d_\lambda^\kappa$ is a depth of a $\lambda^{th}$ soil layer of a control soil sample at a $\kappa^{th}$ control reference point, and λ a quantity of soil layers in the control soil sample;

S52: calculating a flatness p of the soil layer of the target control area by using the soil layer depth data set:

$$p = \frac{1}{\kappa} \sum_{I=1}^{\kappa} \left( \frac{1}{\lambda} \sum_{i=1}^{\lambda} \left| \frac{d_i^\kappa - \hat{d}}{\hat{d}} \right| \right);$$

wherein $d_i^\kappa$ is a depth of an $i^{th}$ soil layer of the control soil sample at the control reference point, i is a number of the soil layer in the control soil sample, I is a number of the control reference point, and $\hat{d}$ is a theoretical depth of the control soil layer; the flatness of the soil layer represents the flatness of the land in the target control area, the flatter the land is, the more conducive it is to plant growth and the more resistant it is to wind-water complex erosion, the uneven the land is, the more easily it is affected by wind-water complex erosion;

S53: calculating average soil viscosity n', moisture content s' and organic matter content y' of control soil samples at a $\kappa^{th}$ control reference point by using the method of the step S2, substituting the average soil viscosity n', moisture content s' and organic matter content y' into the fitted relationship model, and calculating the soil-binding coefficient g' of the target control area;

S54: matching an optimal soil-binding plant around data acquisition reference points in the historical control area according to the soil-binding coefficient g', minimizing a difference between the soil-binding coefficient $g_{max}$ corresponding to the optimal soil-binding plant and the soil-binding coefficient g', and obtaining a planting density ρ of the optimal soil-binding plants in the historical control area; and S55: calculating the soil and water loss coefficient u under the current planting density ρ:

$u = g_{max} - \mu_1 \cdot \exp^p + \mu_2 \cdot \exp^\rho$;

wherein $\mu_1$ is a weight coefficient of the flatness of the soil layer related to the soil and water loss, and $\mu_2$ is a weight coefficient of the plant planting density related to the soil and water loss.

S6: Setting a soil and water loss coefficient threshold $u_{threshold}$;

if $u \geq u_{threshold}$, planting optimal soil-binding plants in the target control area according to a planting density ρ, and controlling the soil and water loss in the wind-water complex erosion region; and if $u < u_{threshold}$, increasing a planting density to ρ+Δρ to enable $u \geq u_{threshold}$, planting optimal soil-binding plants in the target control area according to the planting density ρ+Δρ, and controlling the soil and water loss in the wind-water complex erosion region, wherein Δρ is an increased planting density.

The present invention is used to research the soil and water loss control in the wind-water complex erosion region; specifically, plants with the optimal soil-binding effect are selected through researching the control effect in the historical control area and matches plant types adaptive to a target control area, a planting density is set, the control effect of the plants on the target control area is evaluated according to a calculated soil and water loss coefficient, and the soil-binding effects of different plants on the target control area is considered from multiple aspects, so that the optimal soil and water loss control effect is ensured.

What is claimed is:

1. A method for controlling soil and water loss in a wind-water complex erosion region, comprising the following steps:
S1: randomly selecting a data acquisition reference point in a historical control area, uniformly selecting a plurality of data acquisition points around the data acquisition reference point, and acquiring a soil sample of a set depth at each of the data acquisition points;
S2: detecting soil data of different soil layers on the soil sample, comprising soil viscosity, moisture content and organic matter content, and calculating average soil viscosity $\bar{n}$, moisture content $\bar{s}$ and organic matter content $\bar{y}$ of the soil samples around the data acquisition reference point;
S3: selecting a nearest plant at each data acquisition point as a plant sample, acquiring the plant sample by directly uprooting the plant, calculating a solid-binding coefficient of the plant sample, and selecting an optimal soil-binding plant around the data acquisition reference point;
S4: establishing a relationship model between the soil-binding coefficient and the soil viscosity, moisture content and organic matter content, and fitting the relationship model;
S5: acquiring a control soil sample in a target control area of the wind-water complex erosion region, calculating a flatness of a soil layer of the target control area according to a depth of a soil layer on each control soil sample, and substituting soil viscosity, moisture content and organic matter content of the control soil samples into a fitted relationship model to obtain a soil-binding coefficient of the target control area; further calculating a soil and water loss coefficient u;
S6: setting a soil and water loss coefficient threshold $u_{threshold}$;
if $u \geq u_{threshold}$, planting optimal soil-binding plants in the target control area according to a planting density $\rho$, and controlling the soil and water loss in the wind-water complex erosion region; and
if $u < u_{threshold}$, increasing a planting density to $\rho + \Delta\rho$ to enable $u \geq u_{threshold}$, planting optimal soil-binding plants in the target control area according to the planting density $\rho + \Delta\rho$, and controlling the soil and water loss in the wind-water complex erosion region, wherein $\Delta\rho$ is an increased planting density;
the step S3 specifically comprises:
S31: selecting a nearest plant at each data acquisition point as a plant sample, acquiring the plant sample by directly uprooting the plant, measuring a length L and a distribution radius r of a retained root system and a weight t of soil adhering to the root system in the plant sample, and calculating a soil-binding coefficient $g_e$ of each plant sample:

$$g_e = \exp^{(L+r+t)};$$

S32: after calculating soil-binding coefficients ($g_1$, $g_2$, ..., $g_e$) of all plant samples around the data acquisition reference point, selecting a maximum value $g_{max}$ in the soil-binding coefficients ($g_1$, $g_2$, ..., $g_e$), and taking a plant sample corresponding to the maximum value $g_{max}$ as the optimal soil-binding plant around the data acquisition reference point, wherein e is a quantity of plant samples;

the step S5 specifically comprises:
S51: uniformly selecting $\kappa$ control reference points in the target control area of the wind-water complex erosion region, acquiring control soil samples on the control reference points, and measuring depths of soil layers sequentially descending from a surface soil layer to a highest point in the control soil samples by taking a highest point in the control reference points as a reference to obtain a soil layer depth data set:

$$\{(d_1^1, d_2^1, \ldots, d_\lambda^1)_1, (d_1^2, d_2^2, \ldots, d_\lambda^2)_2, \ldots, (d_1^\kappa, d_2^\kappa, \ldots, d_\lambda^\kappa)_\kappa\};$$

wherein $d_\lambda^\kappa$ is a depth of a $\lambda^{th}$ soil layer of a control soil sample at a $\kappa^{th}$ control reference point, and $\lambda$ a quantity of soil layers in the control soil sample;
S52: calculating a flatness p of the soil layer of the target control area by using the soil layer depth data set:

$$p = \frac{1}{\kappa}\sum_{I=1}^{\kappa}\left(\frac{1}{\lambda}\sum_{i=1}^{\lambda}\left|\frac{d_i^\kappa - \hat{d}}{\hat{d}}\right|\right);$$

wherein $d_i^\kappa$ is a depth of an $i^{th}$ soil layer of the control soil sample at the control reference point, i is a number of the soil layer in the control soil sample, I is a number of the control reference point, and $\hat{d}$ is a theoretical depth of the control soil layer;
S53: calculating average soil viscosity n', moisture content s' and organic matter content y' of control soil samples at a $\kappa^{th}$ control reference point by using the method of the step S2, substituting the average soil viscosity n', moisture content s' and organic matter content y' into the fitted relationship model, and calculating the soil-binding coefficient g' of the target control area;
S54: matching an optimal soil-binding plant around data acquisition reference points in the historical control area according to the soil-binding coefficient g', minimizing a difference between the soil-binding coefficient $g_{max}$ corresponding to the optimal soil-binding plant and the soil-binding coefficient g', and obtaining a planting density $\rho$ of the optimal soil-binding plants in the historical control area; and
S55: calculating the soil and water loss coefficient u under the current planting density $\rho$:

$$u = g_{max} - \mu_1 \cdot \exp^p + \mu_2 \cdot \exp^\rho;$$

wherein $\mu_1$ is a weight coefficient of the flatness of the soil layer related to the soil and water loss, and $\mu_2$ is a weight coefficient of the plant planting density related to the soil and water loss.

2. The method for controlling the soil and water loss in the wind-water complex erosion region according to claim 1, wherein the step S2 specifically comprises:
detecting soil data of different soil layers on the soil sample, comprising soil viscosity, moisture content and organic matter content, and calculating average soil viscosity $\bar{n}$, moisture content $\bar{s}$ and organic matter content $\bar{y}$ of the soil samples around the data acquisition reference point;

$$\bar{n} = \sum_{M_2}^{M}\sum_{m_1=1}^{m} n_{m_1}, \bar{s} = \sum_{M_2}^{M}\sum_{m_1=1}^{m} s_{m_1}, \bar{y}_M = \sum_{M_2}^{M}\sum_{m_1=1}^{m} y_{m_1};$$

wherein M is a quantity of data acquisition points, m is a quantity of soil layers in the soil sample, $n_{m_1}$ is soil viscosity of an $m_1{}^{th}$ soil layer in the soil sample, $m_1$ is a number of the soil layer in the soil sample, $s_{m_1}$ is soil moisture content of an $m_1{}^{th}$ soil layer in the soil sample, $y_{m_1}$ is soil organic matter content of an $m_1{}^{th}$ soil layer in the soil sample, and $M_2$ is a number of the data acquisition point around the data acquisition reference point.

3. The method for controlling the soil and water loss in the wind-water complex erosion region according to claim 1, wherein the step S4 specifically comprises:

S41: establishing a relationship model between the soil-binding coefficient and the soil viscosity n, moisture content s and organic matter content y;

$g = k_1 n + k_2 s + k_3 y;$ wherein $k_1$, $k_2$ $k_3$ are relationship coefficients corresponding to the soil viscosity, moisture content, and organic matter content;

S42: substituting the maximum value $g_{max}$ and the average soil viscosity $\vec{n}$, moisture content $\vec{s}$ and organic matter content $\vec{y}$ of corresponding data acquisition reference points into the relationship model, selecting at least three data acquisition reference points in the historical control area, and fitting out the relationship coefficients $k_1$, $k_2$ $k_3$ to obtain a fitted relationship model.

* * * * *